United States Patent [19]

Engländer et al.

[11] 3,987,117

[45] Oct. 19, 1976

[54] PROCESS FOR PURIFYING VINYL FLUORIDE

[75] Inventors: Fritz Engländer, Bonn-Bad Godesberg; Gunther Meyer, Troisdorf-Sieglar, both of Germany

[73] Assignee: Dynamit Nobel Aktiengesellschaft, Troisdorf, Germany

[22] Filed: Apr. 24, 1974

[21] Appl. No.: 463,918

[30] Foreign Application Priority Data

Apr. 26, 1973  Germany............................ 2321121

[52] U.S. Cl........................... 260/653.3; 260/656 R; 260/42.27
[51] Int. Cl.$^2$.................... C07C 21/18; C07C 17/38
[58] Field of Search...................... 260/653.3, 656 R

[56] References Cited

UNITED STATES PATENTS

| | | | |
|---|---|---|---|
| 2,407,405 | 9/1946 | Dietrich et al. | 260/652.5 P |
| 2,889,378 | 6/1959 | Boettger et al. | 260/653.3 |
| 3,737,471 | 6/1973 | Paucksch et al. | 260/653.3 |
| 3,804,910 | 4/1974 | Furrow | 260/653.3 |

FOREIGN PATENTS OR APPLICATIONS

180,188   4/1966   U.S.S.R............................. 260/656

*Primary Examiner*—D. Horwitz
*Attorney, Agent, or Firm*—Burgess, Dinklage & Sprung

[57] ABSTRACT

Vinyl fluoride having an impurities content of less than 100 parts per million; a method of preparing vinyl fluoride with an impurities content of less than 100 parts per million which comprises contacting gaseous vinyl fluoride with a finely divided copper containing catalyst composition at a temperature of between 0° and 100° C.; a polyvinyl fluoride organosol having an organosol viscosity, determined in a 40 wt.% suspension in propylene carbonate of 20 to 100 cP; a method of producing a polyvinyl fluoride which when suspended in a suspension in polypropylene carbonate in an amount of 40 wt.% has an organosol viscosity of about 20 to 100 cP. which comprises heating vinyl fluoride in an aqueous medium containing a water soluble azo initiator at a pressure less than 140 kp./cm$^2$ at a temperature of 60°–85° C.

8 Claims, No Drawings

PROCESS FOR PURIFYING VINYL FLUORIDE

BACKGROUND OF THE INVENTION

1. Field of the Invention

This invention relates to the preparation of refined and purified vinyl fluoride. More particularly, this invention relates to the preparation of purified gaseous vinyl fluoride which, when subjected to polymerization at a pressure less than 140 kp./cm$^2$ employing a water soluble azo initiator catalyst at 60°–85° C. provides a polyvinyl fluoride which, when employed as a 40 wt. percent suspension in propylene carbonate has an organosol viscosity of about 20 to 100 cP. More especially, the present invention is directed to the preparation of polyvinyl fluoride polymers which are particularly useful as coating agents especially when employed in a suspension in a latent solvent.

2. Discussion of the Prior Art

Vinyl fluoride polymers have excellent resistance to weathering and chemicals and therefore they are widely used for coating surfaces exposed to corrosion such as iron, aluminum and the like. The coating is best performed by applying to the surface to be protected a suspension of polyvinylfluoride in suitable high-boiling diluent such as propylene carbonate or $\gamma$-butyrolactone, with the addition of pigments, fillers, stabilizers etc. if desired, and heating it to temperatures above 200° C., whereupon the polyvinylfluoride particles softened by the liquid flow together and form a non-porous, adherent coating. At the same time the organic liquid evaporates and a coating that is free of solvent is achieved. The high-boiling diluents are also referred to as latent solvents. Latent solvents other than propylene carbonate or $\gamma$-butyrolactone may be used, e.g., those listed in DAS No. 1,546,896, page 10.

The economy of this procedure depends to a great extent on the amount of latent solvent that is needed in order to produce a suspension that is sufficiently fluid for the coating. The lower the amount of latent solvent can be kept, the more useful a polyvinylfluoride will be for surface coating. For this purpose, however, it is necessary to prepare polyvinylfluoride with a low organosol viscosity. Hitherto, high pressures of more than 141 kg/cm$^2$ have been necessary for the production of such vinyl fluoride polymers (cf. DT-OS No. 1,745,748).

It has become desirable to provide a polyvinylfluoride polymer which when employed as a suspension in a latent solvent has a low organosol viscosity. Thus, it has become desirable to provide a refined vinyl fluoride monomer which, when polymerized, provides a polyvinylfluoride polymer which, when in suspension, has a low organosol viscosity. It has thus become desirable to provide a relatively pure vinyl fluoride monomer which can be polymerized to provide a polyvinyl fluoride polymer with the desired physical properties.

SUMMARY OF THE INVENTION

The long felt desideratums in the field of vinyl fluoride monomer synthesis and in the field of polyvinylfluoride synthesis are answered, in accordance with the present invention which provides a process for the purification of gaseous vinyl fluoride which process comprises contacting said gaseous vinyl fluoride with a finely divided copper containing catalyst at a temperature of between 0° and 100° C.

It has thus been discovered, in accordance with the present invention, that by contacting gaseous vinyl fluoride with a copper catalyst, particularly a copper catalyst which has been prereduced with hydrogen, that gaseous vinyl fluoride can be purified to an impurities content of less than 100 parts per million. Moreover, it has been discovered that highly desirable polyvinylfluoride can be obtained using a vinyl fluoride monomer of impurities content of less than 100 parts per million. Especially it has been found that polyvinylfluoride of low organosol viscosity can be prepared by polymerization in an aqueous medium at pressures less than 140 kps./m$^2$. Thus, the present invention contemplates a process for the polymerization of vinylfluoride which process comprises contacting said vinylfluoride in an aqueous medium containing a water soluble azo initiator at a pressure less than 140 kps./cm.$^2$ at a temperature of 60° to 85° C. Polyvinylfluoride recovered from such a polymerization has been found, unexpectedly, to possess highly desirable properties rendering particularly useful as a coating material. Thus, polyvinylfluorides obtained by such polymerization using a vinyl fluoride monomer of impurities content of less than 100 parts per million provide, when suspended in an organosol, a polyvinylfluoride organosol having an organosol melt viscosity of between 20 and 100 cP. The net result is that coating compositions comprising the polyvinylfluoride and an organosol require far less latent solvent or dispersant. Thus, the organosol dispersant composition is far more economical in that less solvent is required. It will be recalled that substantial quantities of the solvent are lost during the coating operation wherein elevated temperatures are utilized to soften dispersed polyvinylfluoride and to remove the latent solvent-dispersant.

DISCUSSION OF PREFERRED EMBODIMENTS

It has been found that vinyl fluoride polymers of low organosol viscosity can be produced in a polymerization process employing pressures of less than 140 kps./cm.$^2$ using as the monomer an especially refined vinyl fluoride. The subject of the present invention thus begins by providing a process for the removal of impurities in gaseous vinyl fluoride which process involves contacting gaseous vinyl fluoride, such as vinyl fluoride prepared by conventional methods with a copper containing catalyst in a finely divided form at temmperatures between 0° and 100° C., preferably between 20° and 60° C.

In particularly desirable embodiment the gaseous vinyl fluoride is subjected to a preliminary refinement by distillation and is stabilized by the addition of a suitable stabilizer prior to such time that it is brought into contact with the finely divided copper catalyst.

The vinyl fluoride can be prepared by any of several known means. For example it can be obtained by the hydrofluorination of acetylene in the method described in U.S. Pat. No. 2,118,901. It can also be obtained by the dehydrofluorination of 1,1-difluoroethane or by other methods of preparation such as described in U.S. Pat. Nos. 2,480,560, 2,599,631 and 2,674,632.

It is also known that oxygen and acetylene generally constitute undesirable impurities in gaseous vinyl fluoride stream. As is apparent from German Offenlegungschrift No. 1,745,748, it has generally been held that these impurities in amounts up to 1,000 parts per million do not interfere with the polymerization process. As a precautionary measure to forstall the possibility of controlled spontaneous polymerization reactions, a stabilizing agent, preferably d,1-limonene, is usually added to commercially available vinyl fluoride made by conventional processes.

The finely divided copper catalyst used in accordance with the invention can be prepared by numerous means such as those described in "Handbuch der präparativen anorganischen Chemie" by G. Brauer, second edition, pages 412 et seq. The article discloses the preparation of reduced finely divided copper catalysts by first reacting copper chloride with a base, washing and drying to get copper oxide which is then reduced with hydrogen. A finely divided copper prepared by reduction with hydrogen at elevated temperatures, preferably between 120° and 200° C., of a product which is commercially obtainable under the name "R 3-11" of Badische Anilin- und Sodafabrik has been found to be an especially effective reduced finely divided copper material for the purification of gaseous vinyl fluoride. This product is mainly a mixture of silica and copper carbonate ($CuCO_3$).

In the method of the invention for the removal of impurities from vinyl fluoride, one may proceed by filling a vertical tube having a diameter of 100 mm. and a length of 300 mm. with an unreduced copper catalyst. For example, the tube can be closed at one or, if desired, both ends by a supporting sieve. At temperatures between 120° and 200° C., the copper catalyst is reduced by passing hydrogen therethrough. Hydrogen gas occupying the interstices between the copper catalyst is displaced at the commencement of the vinylfluoride purification by the passage of the vinyl fluoride therethrough. After the hydrogen has been removed, the gaseous vinyl fluoride that is to be refined is passed through the tube at a rate of 1 kg. per minute at temperatures between 0° and 100° C., preferably between 20° and 60° C.

The refining process can also be performed by passing vinyl fluoride through a catalyst that is in solid form. The vinyl fluoride thus refined can be transferred into an autoclave for subsequent polymerization. Depending upon the quantity and nature of the impurities, approximately 1.5 metric tons of vinyl fluoride can be refined with about 3 kgs. of catalyst, e.g. reduced R 3-11 before it is necessary to regenerate or replace the proper catalyst. By performing the vinyl fluoride purification in the manner described above using a reduced copper catalyst the impurities content of the vinyl fluoride can be remarkably reduced thus preparing this material for a polymerization step at a pressure less than 140 kps./$cm.^2$, when a low organosol viscosity is desired. Generally speaking, the impurities content which acts as inhibitors for polymerization of the vinyl fluoride monomer recovered from the purification process is such that it optionally contains only 20–50 parts per million impurities.

The refining effect can be intensified by subjecting the vinyl fluoride additionally to a refinement by means of inert solids having a large specific surface area. A porous silica gel has proven especially effective, preferably one having a specific surface area of about 10 to 1,000 $m^2$/gm. measured by the BET method. The inert solvents are used preferably in the form of beads of a size of about 1 to 5 mm. in diameter. Active charcoal, clay, calcium phosphate and other such inert solids have a specific surface area within the stated range above and having properties similar to silica gel can also be used as inert solids.

It has also been found advantageous, in accordance with the present invention, to subject a vinyl fluoride which has been provided with a stabilizer (e.g., d,1-limonene of 0.1 wt.%) first to a refinement by means of the inert solids of high specific surface area by placing it in contact with the finely divided copper. In this manner, the life of the copper catalyst can be extended.

If the vinyl fluoride contains no stabilizer, a good refining effect is achieved in the refinement by means of a finely divided copper catalyst alone. However, additional refinement with inert solids is preferred, for purposes of achieving optimum purification. The inert solid can be brought into contact with the vinyl fluoride in much the same manner as the copper catalyst. Surprisingly, a vinyl fluoride of improved purity is obtained by the process of the present invention. The content of impurities amounts, in accordance with the invention, to be less than 100 parts per million and preferably within the range of 20–50 parts per million.

The term "impurities" is intended to include both the stabilizers added afterward to the finished vinyl fluoride and the foreign substances which enter it due to circumstances involved in its preparation. Undesirable foreign substances have proven, on the basis of gas chromatographic analysis, to be mainly molecular oxygen, sulfur compounds such as mercaptans, for example, and acetylene. Additional undesirable accompanying substances which are not listed here and which cannot be analyzed by the methods known to date are also to be considered as impurities.

It has been found that it is desirable to free the vinyl fluoride of molecular oxygen to the greatest possible extent. At a content of more than 25 parts per million, products of uniform quality are not obtained in the subsequent polymerization. Accordingly, in the presence of more than 25 parts per million, reproducibility is lost. By the method of the invention a vinyl fluoride may be obtained which contains less than 25 parts per million of molecular oxygen.

Additional subject matter of the invention is the use of the refined vinyl fluoride as a monomer for the preparation of polyvinylfluoride having a low organosol viscosity through polymerization in an aqueous medium in the presence of water-soluble azo compounds as initiators, at temperatures above the critical temperature, preferably at 60° to 85° C., and at pressures of less than 140 kg/$cm^2$, preferably at pressures of 35 to 80 kp/$cm^2$, and especially at 40 to 60 kp/$cm^2$.

The polymerization of the refined vinylfluoride takes place in an aqueous medium in the presence of water-soluble azo compounds as initiators.

By conducting the process at a pressure of less than 140 kp./$cm^2$ there is obtained a polyvinyl fluoride polymer of unusual properties. This polyvinyl fluoride polymer can be dispersed in a latent solvent such as propylene carbonate. The resultant dispersion has a remarkably lower organosol viscosity than that which would be obtained if the polymerization were carried out by art recognized techniques using an unrefined vinyl fluoride. The organosol viscosity of the polyvinyl fluorides is determined by forming a suspension of polyvinyl fluoride in propylene carbonate. 40 gm. of polyvinyl fluoride are mixed with 60 gms. of propylene carbonate and stirred with a high-speed stirrer until a homogeneous mixture is formed. Then the mixture is temperature controlled at precisely 25° C. by immersion in a water bath. The viscosity measurement is performed in a "HaaKe-Rotovisco" with a MV1 measuring system and with a shear gradient $D = 126$ sec.$^{-1}$.

Using the vinyl fluoride refined in accordance with the invention as monomer, the polyvinylfluoride so produced has an organosol viscosity, determined in a 40 wt.% suspension in propylene carbonate of about 20 to 100 cP, preferably 25–50 cP. This contrasts sharply with organosol viscosities calculated for 40% solutions of art prepared polyvinylfluoride utilizing unrefined vinyl fluoride monomer. These art prepared polyvinylfluorides have organosol viscosities in excess of 400 such as 510 cP.

The polymerization is started by water-soluble azo compounds which degrade into radicals at elevated temperature. Preference is given to the use of $\alpha,\alpha'$-azo-bis-isobutyramidine 2 HCl. The polymerization is generally conducted for a period of time between 100 and 250 minutes, preferably between 120 and 160 minutes per 35 kgs of VF. The polymerization is usually conducted until the vinyl fluoride added to the polymerization system is consumed and a sample of the polyvinylfluoride so recovered is shown to have a melt flow number of between 7 and 11.

The polymerization is performed preferably at 60° to 85° C., especially at 70° to 80° C. small particles with a diameter of about 0.1 to 0.15 $\mu$ are obtained (at a solid concentration of 12 wt.%). Upon completion of the preparation of such a latex, organosols of higher viscosity are obtained. Since, however, it is desirable to prepare a latex in which the particles have a larger diameter, it is preferable to operate at temperatures of approximately 70 to 80° C. and at solid concentrations between about 9 to about 14 wt.%, especially 12 wt.%. In this procedure, and by sustaining the pressure conditions in accordance with the invention, particles of which 95% have a diameter of at least 0.32 $\mu$ are obtained. If the polymerization temperatures are below 60° C., the polymerization still takes place, but the speed of the reaction becomes so slow that the process is uneconomical.

The polymerization can be performed continuously or discontinuously. In the continuous process it is preferable to feed in water in addition to vinyl fluoride and initiator during the reaction and draw off the polymer latex at the bottom of the autoclave in such quantity that the same fill level will always be maintained in the reactor.

The latex drawn off is subjected preferably to spray drying, preferably at air temperatures between 65° C. and 190° C. In this manner one obtains polyvinylfluoride agglomerates which are easily broken up and which, in a 40 wt.% suspension in propylene carbonate, have an organosol viscosity of 20 to 100 cP, preferably 25 to 50 cP. The melt flow number of the polyvinylfluorides amounts to 7 to 11. The melt flow number is determined as follows:

1.00 g of polyvinylfluoride is compressed in a mold in a tableting press at room temperature at a load of 500 kp, so that a tablet with a diameter of 25.4 mm. is formed. The tablet is then pressed for 5 minutes between two chromium-plated steel plates at 260° C. under a load of 5550 kp. During the pressing the temperature is not to vary by more than ± 1° to 20° C. When the polyvinylfuoride melts the pressure in the press drops slightly and must be pumped back up to 5550 kp. After 5 minutes the plates are cooled by immersion in cold water. The diameter of the polyvinylfluoride disk thus obtained is precisely measured. The melt flow number is defined as: $MFN = (dn/dv)^2$; $dv$ represents diameter before pressing at 260° C (25.4 mm); $dn$ represents diameter in mm. after pressing at 260° C.

The determination of the particle size is performed directly on the produced latex by means of the electron microscope at a magnification of 25,000 to 30,000x.

The impurities in the vinyl fluoride are determined by gas chromatography.

In order to more fully illustrate the nature of the invention and the manner of practicing the same the following examples are presented.

EXAMPLE 1

A vertically disposed high-grade steel tube of 100 mm. diameter and 300 mm. length, closed at both ends with a supporting sieve, was filled with a silica gel made by Kali-Chemie and obtainable commercially under the name KC-Perlen. The porous silica gel had an average grain size of about 3.5 mm. The specific surface area was about 700 m$^2$/g., measured by the BET method.

A second vertically high-grade steel tube of approximately the same dimensions, filled with a copper catalyst, was connected to the output of the first tube. The copper catalyst had been made by reducing the product marketed by Badische Anilin- und Soda-Fabrik under the name "R 3-11", by means of hydrogen at temperatures between 120° and about 200° C. The hydrogen was displaced before the catalyst was placed in operation by passing gaseous vinyl fluoride through it. At a rate of flow of 1 kg./min., the commercial vinyl fluoride that was to be refined was passed at a temperature of 50° C. first through the first silica gel-filled tube and then through the second tube filled with the copper catalyst, and then into the autoclave in which the polymerization was to be done. The commercial vinyl fluoride to be refined had been made by the hydrofluorination of acetylene. Then it had been subjected to pressure distillation and stabilized with 0.1 wt.% of d,l-limonene.

The total amount of impurities was determined by gas chromatography to be 200 parts per million, of which the molecular oxygen amounted to about 100 parts per million.

Gas chromatographic analysis of the refined vinyl fluoride fed into the autocalve showed a total of less than 20 parts per million impurities. The molecular oxygen amounted to less than 15 parts per million.

EXAMPLE 2

A high-grade steel autocalve with stirring mechanism and automatic temperature control was charged with 205 weight-parts of de-ionized, O$_2$-free water and heated up to 73° C. Then vinyl fluoride, refined in Example 1, was pumped in producing a pressure of 45 kp/cm$^2$, and the reaction was started by pumping in an aqueous solution of 0.008 weight-parts of $\alpha,\alpha'$-azo-bis-isobutyramidine . 2 HCl. The reaction started immediately. The cooling was started up and additional vinyl fluoride was pumped in. To achieve a constant rate of reaction, 0.007 weight-parts of initiator in an aqueous solution was pumped in during the reaction. After 35 weight-parts of vinyl fluoride had been pumped in the polymerization was stopped by shutting off the monomer feed. The still unreacted vinyl fluoride was blown off. A latex was obtained with a solid content of 13% by weight. The polymer particles had a diameter of 0.36$\mu$. The melt flow number was 9.0. A 40 wt.% mixture of the polyvinylfluoride in propylene carbonate had a viscosity of 23 cP. at 25° C. and a shear gradient of 126 sec$^{-1}$.

EXAMPLE 3

A high-grade steel autoclave with stirring mechanism and automatic temperature control was filled with 195 weight parts of de-ionized, $O_2$-free water at a temperature of 71° C., and a vinyl fluoride refined in accordance with Example 1 was pumped in to produce a pressure of 60 kp/cm$^2$. The reaction was started by adding a solution of 0.012 weight-parts of $\alpha,\alpha'$-azo-bis-isobutyrallylamidine . 2 HCl. To obtain a constant reaction rate, an additional 0.01 weight-parts of initiator in aqueous solution were added in the course of the reaction. After 34 weight-parts of vinyl fluoride had been pumped in, the monomer and initiator feeds were shut off and the polymerization was terminated. After the pressure had been relieved the autoclave contained a latex with a content of 13.4% solid matter by weight. The polymer particles in this case, too, were of very uniform shape and size. The diameter was 0.32$\mu$. The polymer had a melt flow number of 8.9. A 40 wt.% mixture in propylene carbonate had a viscosity of 32 cP at 25° C. and a shear gradient of 126 sec$^{-1}$.

EXAMPLE 4

A high-grade steel autoclave with stirring mechanism and automatic temperature control was filled with 190 weight-parts of de-ionized, $O_2$-free water at a temperature of 70° C., the vinyl fluoride refined as in Example 1 was added to develop a pressure of 75 kp/cm$^2$, and the polymerization was initiated by the addition of 0.007 weight-parts of $\alpha,\alpha'$-azo-bis-isobutyramidine . 2 HCl. To obtain a constant transformation rate, 0.004 weight-parts of initiator were fed in during the reaction. After 35 weight-parts of vinyl fluoride had been added the reaction was interrupted. The latex had a solid content of 13.8 wt.% polyvinylfluoride. The diameter of the polymer particles was 0.36$\mu$. The dried polyvinylfluoride had a melt flow number of 8.2. A 40 wt.% mixture of the polyvinylfluoride with propylene carbonate had a viscosity of 34 cP at 25° C. and at a shear gradient of 126 sec$^{-1}$.

EXAMPLE 5

In a high-grade steel autoclave with stirrer, temperature control and a latex outfeed system, the polymerization was started as in Example 2. After 2 hours the continuous outfeeding of the polyvinylfluoride latex began. At the end of the outfeed system there was mounted a nozzle through which the latex was sprayed in finely atomized form into a spray dryer. At the same time the initiator was injected continuously in such quantity that the reaction rate remained constant.

The level of the charge in the autoclave was kept constant by continuous proportionation of the corresponding amount of water. Within one hour, 110 parts by volume of polyvinylfluoride latax had been removed. The solids content amounted to 9 to 12% by weight. The melt flow number was 8.8 to 9.2. A 40 wt.% mixture of the dry polyvinylfluoride with propylene carbonate had a viscosity of 42 cP at 25° C. and a shear gradient of 126 sec$^{-1}$.

EXPERIMENT FOR PURPOSES OF COMPARISON

A high-grade steel autoclave with stirrer and automatic temperature control was filled with 205 weight-parts of de-ionized, $O_2$-free water at 73° C. and commercial vinyl fluoride (impurity content approx. 200 parts per million, of which 100 parts per million was molecular oxygen) prepared by the hydrofluorination of acetylene, partially refined by pressure distillation and stabilized by the addition of 0.1 wt.% d,1-limonene, was added to develop a pressure of 45 kp/cm$^2$. The reaction was started by the addition of 0.16 weight- parts of $\alpha,\alpha'$-azo-bis-isobutyramidine . 2 HCl. The reaction did not start up until after an induction period of 20 minutes. To obtain a constant reaction rate, 0.017 weight-parts of initiator were fed in during the polymerization. After 35 weight-parts of vinyl fluoride had been pumped in, the initiator and monomer feeds were shut off and the unreacted vinyl fluoride was let off. A latex was obtained with a solids content of 12.9 wt.%. The polymer particles had a diameter of 0.16 to 0.20$\mu$. The melt flow number was 8.8. A 40 wt.% mixture of the dried polyvinyl fluoride in propylene carbonate had a viscosity of 510 cP at 25° C. and a shear gradient of 126 sec$^{-1}$.

What is claimed is:

1. A process for purifying gaseous vinyl fluoride which comprises contacting said gaseous vinyl fluoride with finely divided reduced copper catalysts composition at a temperature of 0° to 100° C.
2. A process according to claim 1 wherein the catalyst is a copper catalyst which catalyst is produced by reduction of silicon and copper carbonate and copper oxide with hydrogen at a temperature of 120° to 200° C.
3. A process according to claim 2 wherein the gaseous vinyl fluoride is contacted at a temperature of between 20° an 60° C.
4. A process according to claim 1 wherein the vinyl fluoride is initially refined by distillation and thereafter brought in contact with the finely divided catalyst composition.
5. A process according to claim 1 wherein to the gaseous vinyl fluoride to be refined there is introduced a stabilizer.
6. A process according to claim 1 wherein the catalyst contains the reduction product of a mixture of $SiO_2$, copper carbonate or copper oxide whereby the reduction is effected with hydrogen at a temperature of 120° to 200° C.
7. A process according to claim 1 wherein the catalyst is selected from the group consisting of a reduced silica-copper carbonate catalyst and a reduced copper oxide catalyst.
8. A process according to claim 1 wherein the catalyst is a finely divided reduced copper catalyst produced by reduction by means of hydrogen of compounds selected from the group consisting of copper oxide, copper chloride, copper sulfate and copper carbonate.

* * * * *

UNITED STATES PATENT AND TRADEMARK OFFICE
CERTIFICATE OF CORRECTION

PATENT NO. : 3,987,117
DATED : OCTOBER 19, 1976
INVENTOR(S) : FRITZ ENGLÄNDER and GUNTHER MEYER It is certified that error appears in the above-identified patent and that said Letters Patent are hereby corrected as shown below:

Column 2, line 47, "temmpera" should read -- tempera- --.
Column 4, line 1, "advantgeous" should read -- advantageous --.
Column 5, line 25, before "small" insert -- Above 85°C. --.

Signed and Sealed this thirtieth Day of August 1977

[SEAL]

Attest:

RUTH C. MASON
Attesting Officer

C. MARSHALL DANN
Commissioner of Patents and Trademarks